(12) United States Patent
Galish et al.

(10) Patent No.: US 6,711,235 B2
(45) Date of Patent: Mar. 23, 2004

(54) X-RAY INSPECTION APPARATUS AND METHOD

(75) Inventors: Andrew Joseph Galish, West Chester, OH (US); Thomas William Birdwell, Middletown, OH (US); Ralph Gerald Isaacs, Cincinnati, OH (US); Francis Howard Little, Cincinnati, OH (US)

(73) Assignee: General Electric Cormpany, Schenectady, NY (US)

( * ) Notice: Subject to any disclaimer, the term of this patent is extended or adjusted under 35 U.S.C. 154(b) by 0 days.

(21) Appl. No.: 10/161,276

(22) Filed: May 31, 2002

(65) Prior Publication Data

US 2003/0223547 A1 Dec. 4, 2003

(51) Int. Cl.$^7$ .................................................. G21K 1/02
(52) U.S. Cl. ........................... 378/147; 378/148; 378/57
(58) Field of Search .................................. 378/147, 148, 378/57, 149, 158, 159

(56) References Cited

U.S. PATENT DOCUMENTS

| | | | |
|---|---|---|---|
| 4,203,037 A | 5/1980 | Gur et al. | 250/505 |
| 4,241,404 A * | 12/1980 | Lux | 378/2 |
| 4,277,684 A | 7/1981 | Carson | 250/445 T |
| 4,489,426 A | 12/1984 | Grass et al. | 378/150 |
| 4,638,499 A | 1/1987 | Eberhard et al. | 378/7 |
| 4,688,242 A | 8/1987 | Ema | 378/154 |
| 4,691,332 A | 9/1987 | Burstein et al. | 378/7 |
| 4,920,552 A * | 4/1990 | Hermens | 378/153 |
| 5,119,408 A | 6/1992 | Little et al. | 378/4 |
| 5,684,851 A * | 11/1997 | Kurbatov et al. | 378/87 |
| 5,684,855 A | 11/1997 | Aradate et al. | 378/4 |
| 5,898,752 A | 4/1999 | Van Der Wal | 378/49 |
| 6,041,101 A * | 3/2000 | Kooy et al. | 378/147 |
| 6,054,712 A * | 4/2000 | Komardin et al. | 250/353.06 |
| 6,122,344 A | 9/2000 | Beevor | 378/88 |
| 6,175,615 B1 | 1/2001 | Guru et al. | 378/149 |
| 6,304,628 B1 | 10/2001 | Steinberg | 378/65 |
| 6,330,300 B1 * | 12/2001 | Siochi | 378/65 |
| 6,496,557 B2 * | 12/2002 | Wilson et al. | 378/21 |

OTHER PUBLICATIONS

D. W. Fitting et al., Monitoring the Solidification of Single-Crystal Castings Using High–Energy X–Ray Diffraction, JOM, Jul. 1999, vol. 51, No. 7, accessed at http://www.tm-s.org/pubs/journals/JOM/9907/Fitting/Fitting–9907.html on Apr. 12, 2002.

* cited by examiner

Primary Examiner—Edward J. Glick
Assistant Examiner—Irakli Kiknadze
(74) Attorney, Agent, or Firm—V G Ramaswamv; Pierce Atwood

(57) ABSTRACT

An X-ray inspection system is provided having an X-ray source and first and second collimators. The first and second collimators are arranged in relation to the source and the target such that the portion of the target actually illuminated by The X-ray beam is substantially equal to the size of a selected inspection zone.

11 Claims, 3 Drawing Sheets

X-RAY INSPECTION APPARATUS AND METHOD

BACKGROUND OF THE INVENTION

This invention relates generally to X-ray inspection systems and more particularly to collimators for such systems.

It is known to use linear detectors with X-ray inspection systems for industrial parts. Linear detectors can provide improved contrast resolution and are thus well suited for digital radiography (DR) and computed tomography (CT). Additionally, improved contrast resolution is achieved by the use of X-ray collimation, which reduces the contribution of scattered X-rays to the resulting image. Ideally, the X-ray source is vertically collimated to provide a flat X-ray beam plane, which defines an inspection zone on the part being inspected. Unfortunately, there is vertical spreading of the X-ray beam from the X-ray focal spot. This exposes the part to X-rays outside of the desired inspection zone which in turn contributes X-ray scatter. To minimize spreading, the size of the source collimator aperture can be reduced, but this can result in vertical masking of the x-ray focal spot, which reduces the effective output of the X-ray source and therefore increases part inspection time. Vertical collimation can also be provided between the target and the X-ray detector, but this approach increases the distance between the part and the detector, which reduces the effectiveness of the collimation. It also reduces the effective field of view of the inspection (and thus the inspectable part size) and increases the effects of focal spot blurring.

Accordingly, there is a need for an X-ray inspection system which incorporates effective collimation while efficiently utilizing the output of the X-ray source.

BRIEF SUMMARY OF THE INVENTION

The above-mentioned need is met by the present invention, which provides an X-ray inspection system having an X-ray source and first and second collimators. The first and second collimators are arranged in relation to the source and the target such that the portion of the target actually illuminated by The X-ray beam is substantially equal to the size of a selected inspection zone.

The present invention and its advantages over the prior art will become apparent upon reading the following detailed description and the appended claims with reference to the accompanying drawings.

BRIEF DESCRIPTION OF THE DRAWINGS

The subject matter that is regarded as the invention is particularly pointed out and distinctly claimed in the concluding part of the specification. The invention, however, may be best understood by reference to the following description taken in conjunction with the accompanying drawing figures in which:

DETAILED DESCRIPTION OF THE INVENTION

Figure 1:
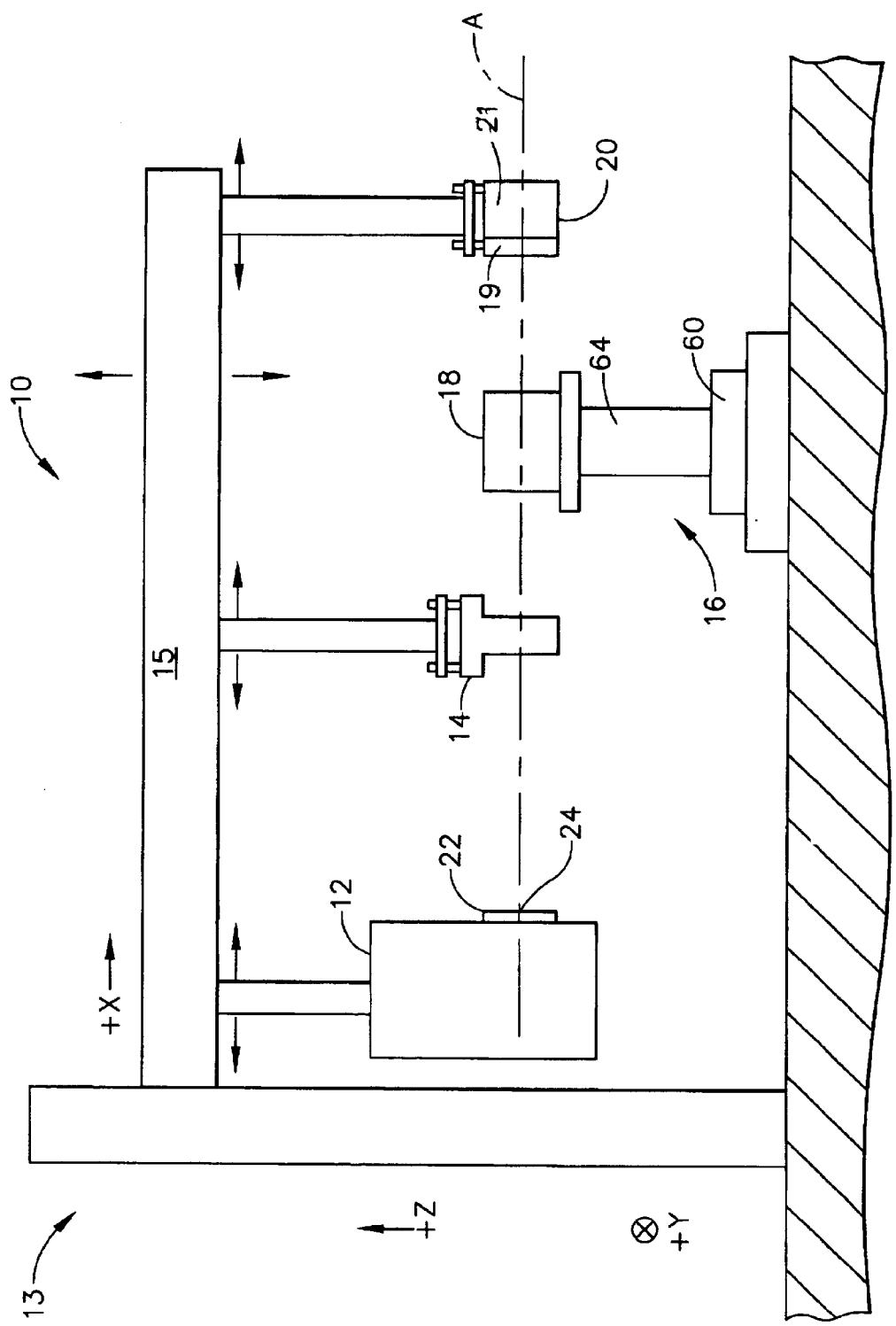
FIG. 1 is a side view of an X-ray inspection system constructed in accordance with the present invention.

Referring to the drawings wherein identical reference numerals denote the same elements throughout the various views, FIG. 1 illustrates an exemplary x-ray inspection apparatus 10 constructed in accordance with the present invention. The apparatus 10 comprises several components disposed sequentially along a central beam axis, denoted A (which is parallel to the x-axis of the overall apparatus), including a high energy X-ray source 12, a pre-target collimator 14, a target support structure 16 which supports a target 18, and a detector assembly 20.

The source 12, pre-target collimator 14, and detector assembly 20 are suspended from a support structure such as a gantry 13 illustrated in FIG. 1 including a horizontal member 15 which may be raised or lowered in a known fashion to move the X-ray components in the vertical or z-direction relative to the target 18. All three of these components may also be moved individually along the x-axis of the apparatus 10 by known means, as indicated by the arrows in FIG. 1.

The X-ray source 12 may be any known X-ray source which is capable of producing X-rays having the energy level required for the particular application. The X-ray source 12 includes a first collimator 22, for example a lead slit-type collimator having an aperture 24 (see FIG. 6) which limits the vertical dispersion of the beam. In the illustrated example the aperture 24 has a vertical dimension (height) of about 3 mm (0.12 in.), and a horizontal dimension (width) of about 100 mm (3.9 in.) One suitable X-ray source is a Linatron M6 linear accelerator of 6 MeV output, available from Varian Industrial Products, 3100 Hansen Way, Palo Alto, Calif., 84104 USA. In an exemplary embodiment, the focal spot of the source 12 is positioned about 2.4 m (96 in.) away from the detector (described below).

Figure 2:
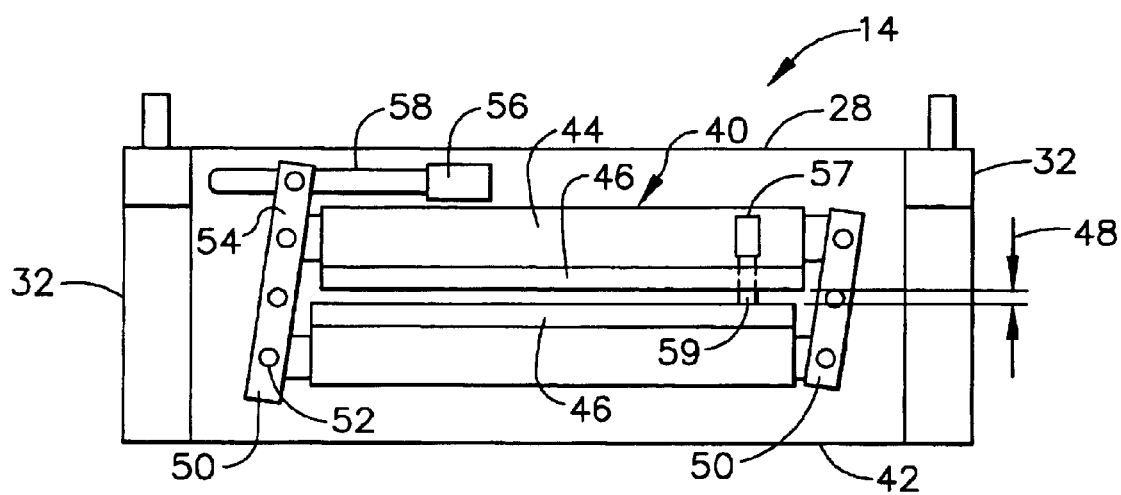
FIG. 2 is a front elevational view of a pre-target collimator suitable for use with the X-ray inspection system of the present invention.
Figure 3:
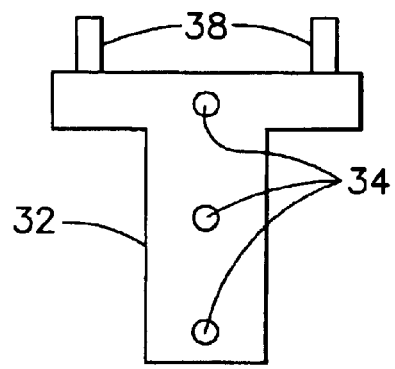
FIG. 3 is a side view taken of the pre-target collimator of FIG. 2.
Figure 4:
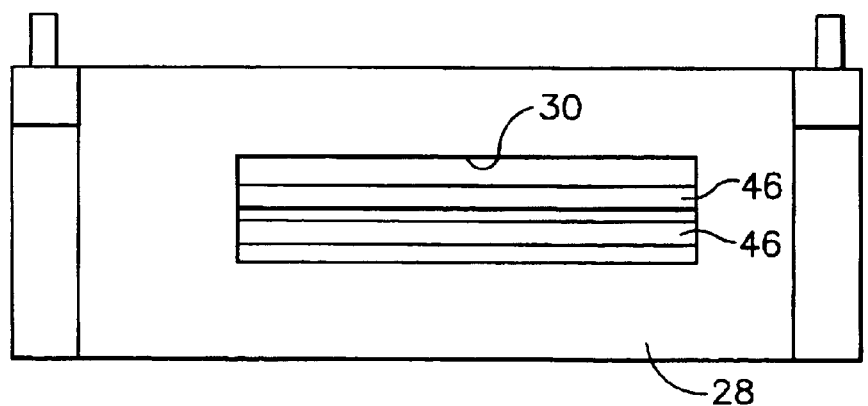
FIG. 4 is a rear elevational view of the pre-target collimator of FIG. 2.

Referring to FIGS. 2, 3, and 4, a pre-target collimator is shown in detail. The pre-target collimator 14 comprises a plate-like body 28 having an opening 30 formed therethrough. A pair of end pieces 32 (see FIG. 3) are attached to each end of the body 28, for example with fasteners 34. The end pieces include a means for attaching the pre-target collimator 26 to a support structure 36, for example with studs 38. A pair of collimator jaws 40 is mounted to the front surface 42 of the body 28. The collimator jaws 40 include a pair of parallel spaced apart bars 44 which each carry a jaw piece 46. The generally rectangular space between the jaw pieces 46 defines the aperture 48 of the pre-target collimator 14. The jaw pieces 46 are constructed of a radio-opaque material, such as tungsten, and have a length sufficient to stop the beam in the x-direction, for example about 7.62 cm (3 in.). The bars 44 are held in parallel, movable relationship to each other by a pair of pivoting links 50, which are attached to the collimator body 28 and the ends of the bars 44 by pivot pins 52. One of the links 50 has an extended arm 54 which is connected to a controllable motor 56 with a pivot pin 50 and a threaded rod 58. This arrangement allows the vertical dimension (height) of the aperture 48 to be adjusted to suit a particular application by operating the motor 56, which causes pivoting of the links 50 which in turn causes the jaw pieces 46 to move towards or away from each other. The operating mechanism of the pre-target collimator 14 includes suitable known means for providing feedback to the means (not shown) used to control the motor 56. For example, a position sensor 57, such as an LVDT, may be mounted on the upper bar 44, with its moveable probe or rod 59 projecting through a hole in the upper jaw piece 46 and contacting the lower jaw piece 46. The output of the position sensor provides a direct measurement of the gap between the jaw pieces 46, and allows control of the aperture 48 independent of any excess motion in the moving parts between the motor 56 and the jaw pieces 46.

In the illustrated example the aperture 48 may be adjusted from approximately 0 mm (0 in.), that is, completely closed, to approximately 6 mm (0.24 in.). The jaws 46 have a width extending in the y-direction (perpendicular to both the x-axis and the z-axis) a distance sufficient to encompass the beam spread at the location of the pre-target collimator 14. In the illustrated example the jaws 36 are approximately 66 cm (26 in.) wide.

The target support structure 16 provides means for supporting and manipulating the target 18. The exemplary support structure 16 illustrated in FIG. 1 comprises a turntable 60 which is powered so as to be able to rotate the target 18. The target 18 is mounted to the turntable with suitable tooling 64, such as a pedestal as shown in the illustrated example. The tooling 64 incorporates known means for securing the target 18, such as clamps or fasteners (not shown). If required, the support structure 16 may also include known means for manipulating the target 18 in other ways, for example rotating the target 18 about other axes than that of the turntable 60, or by moving the target 18 in the x-, y-, or z-axes.

The detector assembly 20 includes an X-ray detector 19, for example a linear array detector 19, and a post-target collimator 21. The post-target collimator is of a known type generally comprising an array of radio-opaque plates arranged to collimate the beam in-plane (i.e. horizontally, or perpendicular to the direction of the first collimator 22 and pre-target collimator 14).

Figure 5:
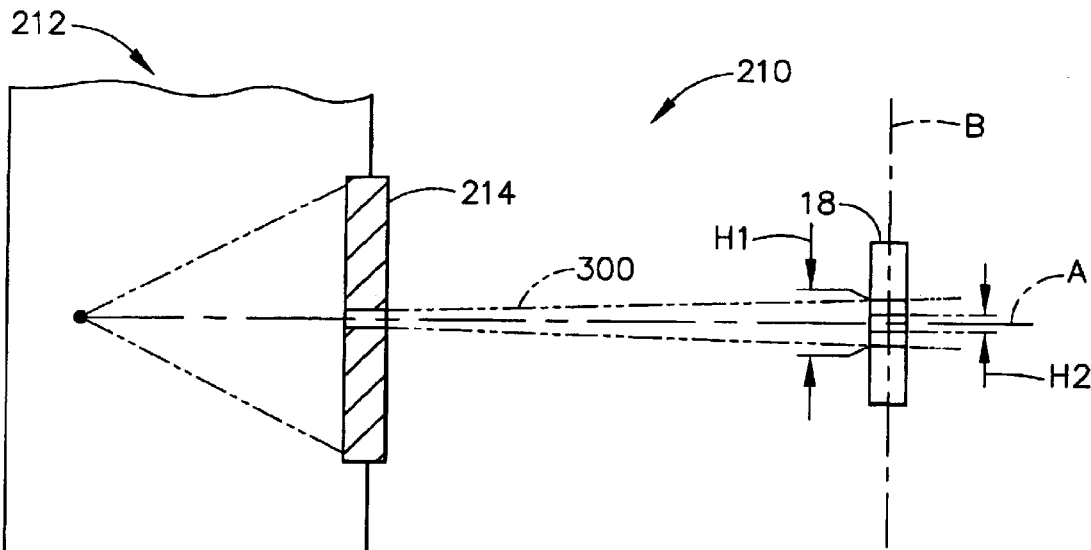
FIG. 5 is a schematic side view of a prior art X-ray inspection system.
Figure 6:
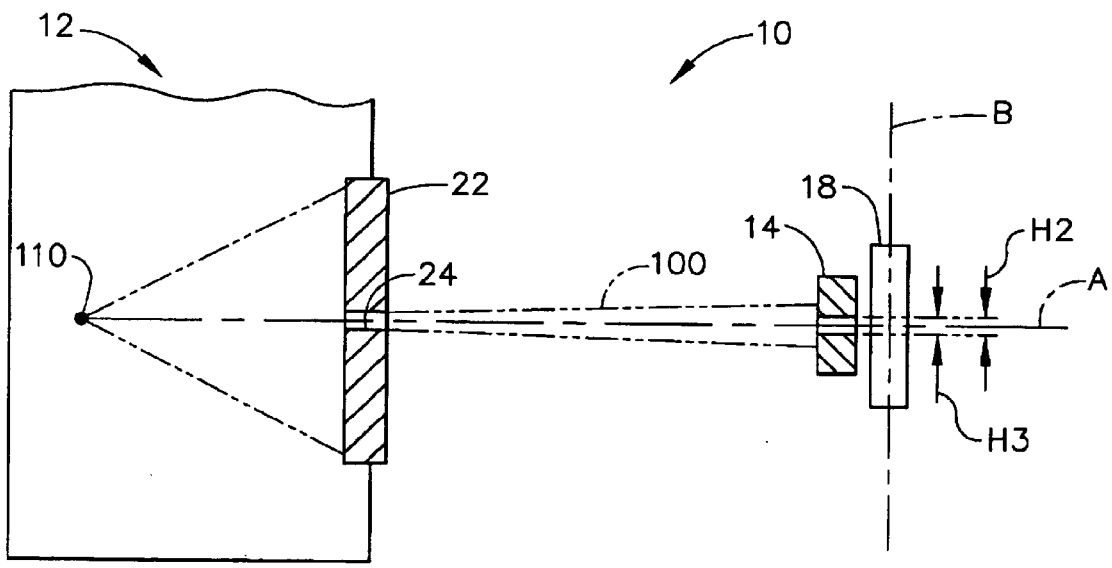
FIG. 6 is a schematic side view of the X-ray inspection system of the present invention.

FIGS. 5 and 6 illustrate the operation of the X-ray inspection apparatus 10 in comparison to that of a prior art system. Referring to FIG. 5, a prior art X-ray inspection system 210 includes a source 212 having a vertical collimator 214. In operation the source 212 produces a fan shaped X-ray beam 300 which diverges as it travels toward a target 18, the centerline of which is denoted B in FIG. 5. This divergence causes the target 18 to be illuminated by X-rays over a zone having a dimension in the z-direction, denoted H1 in FIG. 5. Unfortunately, the z-dimension (height) of the desired inspection zone, denoted H2, is much smaller, for example as small as about 0.5 mm (0.02 in.) The stray radiation outside of the desired inspection zone causes scatter of the X-rays, which degrades both contrast resolution and measurement accuracy of the inspection system.

FIG. 6 illustrates the operation of the X-ray inspection apparatus 10 of the present invention. A x-ray beam 100 is generated in an X-ray source 12. The X-ray beam 100 propagates from a focal point 110 and passes through the horizontal slit aperture 24 of the first collimator 22. The beam 100 then diverges as is travels towards the target 18 along the central beam axis A. The beam 100 subsequently passes through the aperture 48 of the pre-target collimator 14, which is placed as close as physically possible to the target 18. Because the distance from the pre-target collimator 14 to the target 18 is minimized, the portion of the target 18 exposed to the X-ray beam measured in the z-direction, denoted H3 in FIG. 6, is substantially equal to the height H2 of the desired inspection zone, thus eliminating stray radiation and scattering.

In the illustrated example, the pre-target collimator 14 is positioned about 2.5 cm (1 in.) away from the target 18. In comparison, in a similar prior art application not having the pre-target collimator 14, the target 18 is located about 125 cm (49 in.) away from the source collimator. These dimensions are of course merely representative and can be varied to suit a particular application. The important consideration is to locate the pre-target collimator 714 so that it is as close as possible to the target 18 without physically interfering with manipulation of the target 18.

The arrangement of components of the present invention minimizes the collimation requirements at the x-ray source 12 and completely eliminates the need for vertical collimation between the target 18 and the detector assembly 20. In addition, the improved imaging performance of the x-ray inspection apparatus 10 of the present invention enables it to be effectively applied for such applications as composite material and part inspection, reverse engineering of complex parts and assemblies, high resolution x-ray metrology, and first article inspection and validation. An apparatus constructed in accordance with the present invention has shown improvements of as much as 70% in contrast resolution and as much as 40% in measurement accuracy over prior a prior art system, without reducing inspection speed.

The foregoing has described an X-ray inspection system having an X-ray source and first and second collimators, wherein the first and second collimators are arranged in relation to the source and the target such that the portion of the target actually illuminated by The X-ray beam is substantially equal to the size of a selected inspection zone. While specific embodiments of the present invention have been described, it will be apparent to those skilled in the art that various modifications thereto can be made without departing from the spirit and scope of the invention as defined in the appended claims.

What is claimed is:

1. An X-ray inspection system, comprising the following elements disposed sequentially along a central axis:
    an X-ray source capable of projecting a beam of radiation along said central axis;
    a first collimator disposed coaxially with said central axis at a first location along said central axis, said first collimator having a first slit-shaped aperture having a first dimension in a first direction perpendicular to said central axis;
    a second collimator disposed coaxially with said central axis at a second location along said central axis, said second collimator having a second slit-shaped aperture having a second dimension in said first direction; and
    means for causing said central axis to pass through a selected inspection zone of a target, wherein said second location of said second collimator and said second dimension of said second aperture are selected such that the portion of said target actually illuminated by said beam measured in said first direction is substantially equal to the size of said selected inspection zone measured in said first direction.

2. The X-ray inspection system of claim 1 further comprising:
    an X-ray detector disposed adjacent said target and opposite said second collimator; and
    a third collimator disposed between said target and said detector.

3. The X-ray inspection system of claim 2 wherein said third collimator has a third aperture, said third aperture being oriented perpendicular to said central axis and to said first direction.

4. The X-ray inspection system of claim 1 wherein said second dimension of said second aperture is adjustable.

5. A X-ray inspection method, comprising:

provxiding an X-ray source capable of projecting a beam of radiation along a central axis;

providing a first collimator disposed coaxially with said central axis at a first location along said central axis, said first collimator having a first slit-shaped aperture having a first dimension in a first direction perpendicular to said central axis;

providing a second collimator disposed coaxially with said central axis at a second location along said central axis, said second collimator having a second slit-shaped aperture having a second dimension in said first direction;

providing means for causing said central axis to pass through a selected inspection zone of a target, wherein said step of providing said second collimator includes selecting said second location and said second dimension of said second aperture such that the portion of said target actually illuminated by said beam measured in said first direction is substantially equal to the size of said selected inspection zone measured in said first direction.

6. The X-ray inspection method of claim 5 further comprising:

providing an X-ray detector disposed adjacent said target and opposite said second collimator; and providing a third collimator disposed between said target and said detector.

7. The X-ray inspection method of claim 6 wherein said third collimator has a third aperture, said third aperture being oriented perpendicular to said central axis and to said first direction.

8. An X-ray inspection system, comprising the following elements disposed sequentially along a central axis:

an X-ray source capable of projecting a beam of radiation along said central axis;

a first collimator disposed coaxially with said central axis at a first location along said central axis, said first collimator having a first slit-shaped aperture oriented in a first direction;

a second collimator disposed coaxially with said central axis at a second location along said central axis, said second collimator having a second slit-shaped aperture oriented in said first direction; and means for supporting a target, wherein said second collimator is positioned as close as possible to said means for supporting said target without interfering with said target.

9. The X-ray inspection system of claim 8 further comprising:

an X-ray detector disposed adjacent said target and opposite said second collimator; and a third collimator disposed between said target and said detector.

10. The X-ray inspection system of claim 9 wherein said third collimator is oriented perpendicular to said first direction.

11. The X-ray inspection system of claim 8 wherein said second aperture is adjustable is said first direction.

\* \* \* \* \*